(12) United States Patent
Kawase et al.

(10) Patent No.: US 8,257,565 B2
(45) Date of Patent: Sep. 4, 2012

(54) SENSOR CONTROL APPARATUS

(75) Inventors: Tomoo Kawase, Aichi-ken (JP); Eiichi Kurokawa, Okazaki (JP); Toshiyuki Suzuki, Handa (JP); Yohei Kawaki, Toyota (JP)

(73) Assignee: Denso Corporation, Kariya, Aichi-Pref. (JP)

( * ) Notice: Subject to any disclaimer, the term of this patent is extended or adjusted under 35 U.S.C. 154(b) by 1033 days.

(21) Appl. No.: 12/035,206

(22) Filed: Feb. 21, 2008

(65) Prior Publication Data

US 2008/0196480 A1    Aug. 21, 2008

(30) Foreign Application Priority Data

Feb. 21, 2007  (JP) ................... 2007-040959

(51) Int. Cl.
*G01N 27/26* (2006.01)
*G01N 7/00* (2006.01)
(52) U.S. Cl. ...... 204/424; 204/426; 73/23.31; 73/23.32; 73/31.05; 702/104; 701/109
(58) Field of Classification Search .................. 204/410, 204/411, 421–429, 781, 783.5–785, 787; 73/23.31, 23.32, 31.05; 205/781, 783.5–785, 205/787; 701/109; 702/104
See application file for complete search history.

(56) References Cited

U.S. PATENT DOCUMENTS

| | | | | |
|---|---|---|---|---|
| 4,547,281 A | * | 10/1985 | Wang et al. | 204/424 |
| 5,935,400 A | * | 8/1999 | Takami et al. | 204/425 |
| 6,478,940 B1 | | 11/2002 | Suzuki et al. | |
| 2001/0052337 A1 | * | 12/2001 | Suzuki et al. | 123/435 |
| 2002/0050455 A1 | * | 5/2002 | Kurokawa et al. | 204/431 |
| 2004/0195097 A1 | | 10/2004 | Suzuki et al. | |
| 2004/0217001 A1 | * | 11/2004 | Hada et al. | 204/424 |
| 2005/0284759 A1 | * | 12/2005 | Kawase et al. | 204/424 |

FOREIGN PATENT DOCUMENTS

| | | |
|---|---|---|
| JP | 2000-081413 | 3/2000 |
| JP | 2004-251891 | 9/2004 |

OTHER PUBLICATIONS

Hetrick et al., Appl. Phys. Lett. 38(5), 1981, pp. 390-392.*

* cited by examiner

*Primary Examiner* — Jeffrey T Barton
*Assistant Examiner* — Jennifer Dieterle
(74) *Attorney, Agent, or Firm* — Nixon & Vanderhye PC

(57) ABSTRACT

A sensor control apparatus includes an applied voltage control circuit connected to the positive terminal of a sensor element. The applied voltage control circuit includes a reference power supply and a noninverting amplifier circuit connected to the reference power supply. An AC power supply circuit, a buffer and a current measurement resistance are connected in series to the negative terminal of the sensor element with the current measurement resistance disposed between the AC power supply circuit and the sensor element. One terminal of the current measurement resistance, which is on the side opposite to the sensor element, is held at a reference voltage (center voltage of an AC voltage generated from the AC power supply circuit). Voltage at an intermediate point between the current measurement resistance and the sensor element is inputted via a low-pass filter to the noninverting amplifier circuit of the applied voltage control circuit.

7 Claims, 6 Drawing Sheets

SENSOR CONTROL APPARATUS

CROSS REFERENCE TO RELATED APPLICATION

The present application is based on and claims priority from Japanese Patent Application No. 2007-040959, filed Feb. 21, 2007, the content of which is incorporated herein by reference.

BACKGROUND OF THE INVENTION

1. Field of the Invention

The present invention relates to a sensor control apparatus for use with a controlled object formed by a sensor element having a solid electrolytic layer and capable of detecting a specific component concentration in a measured gas over a wide range.

2. Description of the Related Art

In the field of automobile engines, for example, a limit-current type oxygen concentration sensor (also called "air-fuel ratio sensor" referred to as "A/F sensor"), which detects the oxygen concentration in an exhaust gas as a detection object, has already been put into practical use. The oxygen concentration sensor is constructed to have a solid electrolytic layer such as zirconia and outputs an electric current signal corresponding to the oxygen concentration in the exhaust gas whenever a voltage is applied a sensor element.

To accurately detect the oxygen concentration, it is necessary to adequately control the voltage applied to the oxygen concentration sensor (the voltage being hereinafter referred to, for brevity, as "applied voltage"). As for such applied voltage control, various techniques have been proposed. According to one example of such prior proposals, which is disclosed in Japanese Patent Laid-open Publication (JP-A) No. 2000-081413, the gas concentration detecting apparatus includes a current measurement resistance connected to a sensor element so that an electric current signal measured by the current measurement resistance is fed back to perform the control of the applied voltage. Furthermore, in order to suppress oscillation of the applied voltage, the inclination of the applied voltage characteristic curve is set to be smaller than the AC impedance of the sensor element.

However, in the sensor element, due to individual difference, deterioration with age or the like, variation in sensor capacitance may occur, which can vary the gain in the applied voltage control. In this instance, if a desired gain cannot be realized due to such gain variation, the oscillation of the applied voltage may occur. Thus, there is still room for improvement.

SUMMARY

With the foregoing in review, a principal object of the present exemplary embodiment is to provide a sensor control apparatus, which is capable of performing an adequate control of the applied voltage of a sensor element.

A sensor control apparatus according to the present invention is used in combination with the so-called limit-current type sensor element as a controlled object having a solid electrolytic layer and measured with a current measurement resistance an element current flowing through the sensor element when a voltage is applied to the sensor element.

In brief, the sensor control apparatus of the present invention may be represented by an equivalent circuit, which, as shown in FIG. 9(a), includes an applied voltage control circuit M2 for variably controlling a voltage to be applied to a sensor element M1, and a current measurement resistance MS connected to the sensor element M1 in a current path over which an element current flows when the applied voltage is applied under the control of the applied voltage control circuit. One of opposite terminals of the current measurement resistance M3, which is on the side opposite to the sensor element M1, is held at a reference voltage. An element current is measured at an intermediate point X1 between the sensor element M1 and the current measurement resistance M3. The applied voltage control circuit M2 determines the applied voltage (sensor applied voltage) based on a signal representing the measured element current.

In the circuit configuration shown in FIG. 9(a), a frequency transfer function is represented by Equation (1) below and a gain characteristic as an amplitude ratio is represented by Equation (2) below, wherein Cs represents the sensor capacitance component (capacitive reactance), Rs represents the sensor resistance component, and R1 represents the resistance value of the current measurement resistance MS.

$$G(j\omega) = \frac{R_1}{R_1 + R_s + \frac{1}{j\omega C_s}} \quad (1)$$

$$|G(j\omega)| = \frac{R_1}{\sqrt{(R_1 + R_s)^2 + \left(\frac{1}{\omega C_s}\right)^2}} \quad (2)$$

For comparative purposes, a conventional circuit configuration (equivalent circuit) is shown in FIG. 9(b). Unlike the circuit configuration shown in FIG. 9(a), the circuit configuration shown in FIG. 9(b) includes a current measurement resistance M3 connected in series with a sensor element M1 and, at the current measurement resistance M3, a terminal voltage on the side opposite to the sensor element M1 is inputted to an applied voltage control circuit M2. In the illustrated arrangement, the voltage at an intermediate point X2 varies with an element current. The applied voltage control circuit M2 determines the applied voltage (sensor applied voltage) based on a voltage signal appearing at the intermediate point X2. In the circuit configuration shown in FIG. 9(b), a frequency transfer function is represented by Equation (3) below and a gain characteristic as an amplitude ratio is represented by Equation (4) below.

$$G(j\omega) = -\frac{R_1}{R_s + \frac{1}{j\omega C_s}} \quad (3)$$

$$|G(j\omega)| = \frac{R_1}{\sqrt{R_s^2 + \left(\frac{1}{\omega C_s}\right)^2}} \quad (4)$$

The sensor element may cause variation in sensor capacitive reactance (capacitance variation) due to individual difference, deterioration with age, etc. Now comparing the above-mentioned two circuit configurations while taking this point into consideration, we will see the following differences. In the circuit configuration (conventional circuit) shown in FIG. 9(b), the denominator term of the gain characteristic (Equation (4)) represents an impedance of the sensor element shown as separated into a resistance component and a reactance component. This means that the gain characteristic fully depends on the sensor element impedance (denominator term of Equation (4)). It is therefore considered that the gain can be varied with a variation in sensor capacitive reactance.

On the other hand, in the circuit configuration (inventive circuit) shown in FIG. 9(a), the denominator term of the gain characteristic (Equation (2)) includes not only a sensor resistance component but also a current measurement resistance value. This means that the value of a voltage divided through the sensor element resistance component and the current measurement resistance value is reflected into the gain characteristic. Thus, the effect of the sensor capacitive reactance on the gain characteristic is reduced and, hence, the gain variation can be suppressed even when sensor capacitive reactance variation occurs. As a result, the applied voltage control of the sensor element can be performed in an adequate manner.

Preferably, the applied voltage control circuit includes an inverting or a noninverting amplifier circuit to which the element current signal measured at the intermediate point between the sensor element and the current measurement resistance is inputted, and a capacitor connected in parallel to a feedback resistance of an operational amplifier constituting the amplifier circuit.

With this arrangement, the applied voltage control circuit has a low-pass filter (LPF) provided integrally with the amplifier circuit. The LPF is a filter provided for preventing oscillation of the applied voltage. A specific circuit configuration of the applied voltage control circuit referred is shown in a broken-lined block (c) of an equivalent circuit shown in FIG. 6. In this case, a frequency transfer function and a gain characteristic of the applied voltage control circuit 21 are represented by the following Equations (5) and (6), respectively. Reference characters used in Equations (5) and (6) are the same as those shown in the broken-lined block (c) of the equivalent circuit shown in FIG. 6.

$$G(j\omega) = 1 + \frac{R_3}{R_4} \frac{1}{1 + j\omega C_2 R_3} \quad (5)$$

$$|G(j\omega)| = \frac{\sqrt{(R_3 + R_4)^2 + (\omega C_2 R_3 R_4)^2}}{R_4 \sqrt{1 + (\omega C_2 R_3)^2}} \quad (6)$$

According to the gain characteristic shown in Equation (6), the denominator and numerator each include a capacitance (C2) of the LPF. Accordingly, even when variation occurs in the capacitance of the capacitor in the LPF, the effect of the capacitance variation can be suppressed. This will ensure that the LPF can be provided without involving performance degradation caused due to component variations. Thus, oscillation of the applied voltage can be controlled as desired.

Unlike the invention, if a low-pass filter (LPF) is provided independently in a path over which an element current flows when a voltage is applied to a sensor element (for example, when an LPF 58 is provided as shown in FIG. 8), a frequency transfer function and a gain characteristic of the LPF 58 are represented by the following Equations (7) and (8), respectively.

$$G(j\omega) = \frac{1}{1 + j\omega C_1 R_4} \quad (7)$$

$$|G(j\omega)| = \frac{1}{\sqrt{1 + (\omega C_1 R_4)^2}} \quad (8)$$

According to the gain characteristic shown in Equation (8), only the denominator includes a capacitance (C1) of the LPF. Accordingly, if variation occurs in the capacitance of the capacitor in the LPF, the performance will be degraded by the effect of the capacitance variation and, in the worst case, oscillation of the applied voltage will occur.

Preferably, the current measurement resistance is connected to an AC power supply circuit, which outputs an AC voltage periodically changing its polarity with respect to the reference voltage. By thus applying the AC voltage from the AC power supply circuit to the sensor element, an impedance of the sensor element can be detected.

The sensor control apparatus may further include a first signal output section which extracts from the element current signal measured at the intermediate point between the sensor element and the current measurement resistance, a first current component corresponding to a gas concentration (oxygen concentration, for example) in the measured gas and outputs the extracted first current component to an arithmetic device, and a second signal output section which extracts from the element current signal measured at the intermediate point between the sensor element and the current measurement resistance, a second current component corresponding to a resistance component (element impedance) of the sensor element and outputs the extracted second current component to the arithmetic device, wherein the element current signal is introduced through separate routes into the first and second signal output sections.

With this arrangement, an element current, which is a combination of the first current component corresponding to the gas concentration in the measured gas and the second current component corresponding to the resistance component of the sensor element, flows through the sensor element while the AC voltage from the AC power supply circuit is applied to the sensor element. In this instance, the first current component corresponding to the gas concentration in the measured gas is extracted by the first signal output section and outputted therefrom to the arithmetic device and, at the same time, the second current component corresponding to the resistance component of the sensor element is extracted by the second signal output section and outputted therefrom into the arithmetic device. The arithmetic device comprises a microcomputer, for example, and performs arithmetic operations to calculate a gas concentration and an element resistance on the basis of the output signals from the first and second signal output sections.

Since the element current signal is introduced through separate routes into the first and second signal output sections, even when voltage levels to be extracted with respect to the element current signals introduced into the respective signal output sections are different, it is possible to perform suitable signal processing operations (amplification, for example) individually for the respective element current signals. In this instance, a two-stage amplification to adjust the voltage level between the gas concentration component and the element resistance component is not necessary, with the result that both the detection of a gas concentration and the detection of an element resistance can be performed with a high degree of accuracy.

Furthermore, with respect to the detection of a gas concentration and an element resistance, the element current signal is measured by an intermediate point voltage (divided voltage) between the sensor element and the current measurement resistance. Unlike another technique in which the element current signal is measured by a voltage appearing across opposite ends of the current measurement resistance, this arrangement allows for direct introduction of the element current signal without relying on the use of a current-to-voltage converting means such as a differential amplifier. The element resistance detection does not require a differential amplifier and hence is able to simplify the circuit configuration.

Preferably, the first signal output section and said second signal output section include amplifier circuit sections for amplifying the element current signals inputted respectively thereto, wherein amplification factors of the amplifier circuit sections are set individually. With this arrangement, even when the element current signals to be processed at the first and second signal output sections have different voltage levels, the element current signals can be amplified individually in accordance with output ranges (for example, 0 to 5 V) of the corresponding amplifier circuit sections. This will increase the resolution of the gas concentration detection and the element resistance detection.

Preferably, the first signal output section includes a filter means (low-pass filter) for extracting only a direct current component of the element current signal, and an amplifying means for amplifying the element current signal based on a voltage-processing range of a signal input section (including an A/D converter) of the arithmetic device. With this arrangement, it is possible to extract from the element current which is a combination of a current component corresponding to the gas concentration and a current component corresponding to the resistance component of the sensor element, only the current component corresponding to the gas concentration with accuracy, ensuring that the gas concentration can be accurately calculated at the arithmetic device.

Preferably, the second signal output section includes a filter means (high-pass filter) for extracting only an alternating current component of a voltage measured at the intermediate point between the sensor element and the current measurement resistor, and a peak detecting means for detecting a peak value of the alternating current component extracted by the filter means of the second signal output section. With this arrangement, it is possible to extract from the element current, which is a combination of the current component corresponding to the gas concentration and the current component corresponding to the resistance component of the sensor element, only the current component corresponding to the element resistance with accuracy, ensuring that the element resistance can be accurately calculated at the arithmetic device. The second signal output section may further include an amplifying means for amplifying the element current signal based on a voltage-processing range of a signal input section (including an A/D converter) of the arithmetic device.

BRIEF DESCRIPTION OF THE DRAWINGS

Other objects and features of the present invention will become more readily apparent from the following detailed description of the preferred embodiment taken in conjunction with the accompanying drawings in which.

DETAILED DESCRIPTION OF THE PREFERRED EMBODIMENT

Figure 1:
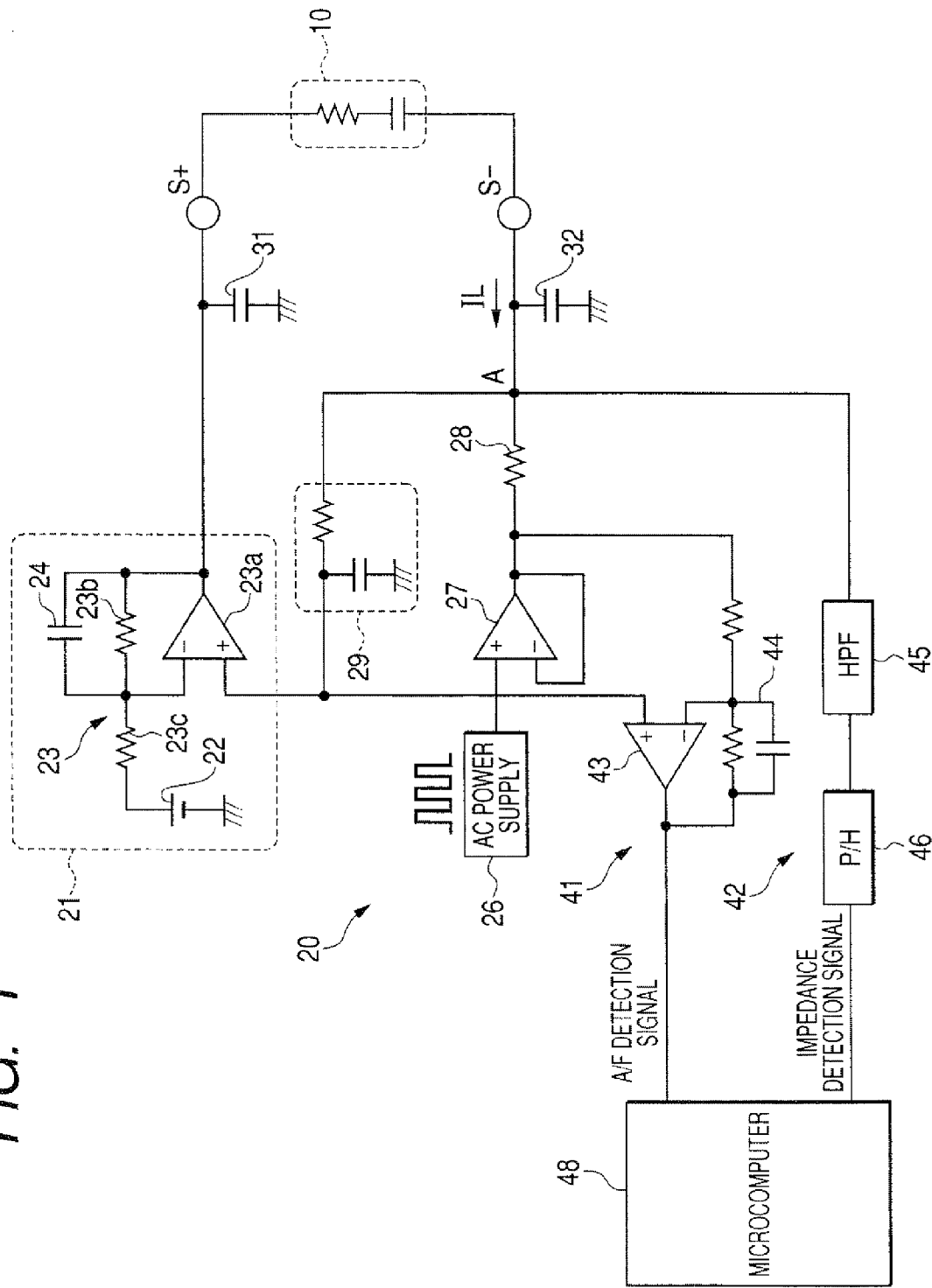
FIG. 1 is a circuit diagram showing the general configuration of a sensor control apparatus according to an embodiment of the present invention.

Referring now to the drawings, a description will be given hereinbelow of a sensor control apparatus according to one preferred embodiment of the present invention. This embodiment relates to an air-fuel ratio detecting apparatus configured to detect an oxygen concentration (air-fuel ratio, which will hereinafter be referred equally to as an "A/F") in a measured gas which is an exhaust gas emitted from an engine mounted on a vehicle, and an air-fuel ratio detection result from the air-fuel ratio detecting apparatus is used in an air-fuel ratio control system comprised of an engine electronic control unit (ECU) and others. In the air-fuel ratio control system, stoichiometric combustion control for feedback-controlling an air-fuel ratio in the vicinity of the stoichiometric air-fuel ratio, lean combustion control for feedback-controlling the air-fuel ratio in a predetermined lean region, or the like control is performed properly.

Figure 2:
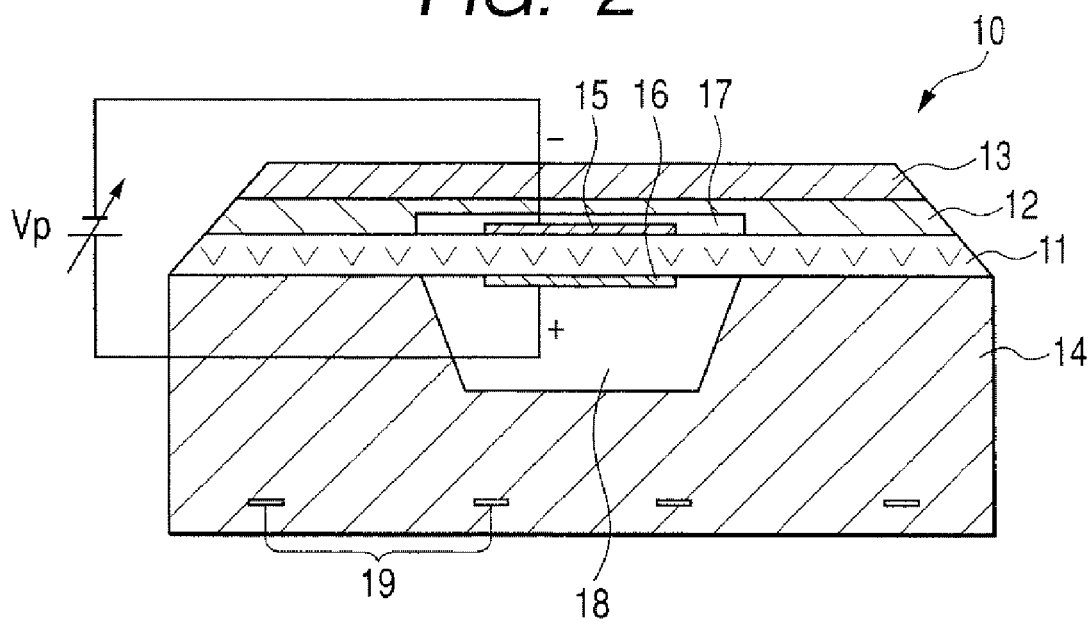
FIG. 2 is a cross-sectional view showing a construction of a sensor element as a controlled object of the sensor control apparatus.

At first, referring to FIG. 2, a description will be given below of a construction of an A/F sensor. The A/F sensor comprises a sensor element 10 having a multilayer construction, and FIG. 2 shows a cross-sectional construction of the sensor element 10. In reality, this sensor element 10 has an elongated configuration extending in a direction perpendicular to the drawing sheet including FIG. 2, and the entire element is accommodated in a housing or an element cover (neither shown).

The sensor element 10 includes a solid electrolytic layer 11, a diffusion resistance layer 12, a shielding layer 13 and an insulating layer 14 which are stacked or laminated one above another as shown in FIG. 2. A protective layer (not shown) is placed around the sensor element 10. The solid electrolytic layer illustrated as a rectangular plate is formed by a partial stabilization zirconia sheet, and a pair of electrodes 15 and 16 are provided opposite to each other with the solid electrolytic layer 11 interposed between the electrodes 15 and 16. The diffusion resistance layer 12 is formed from a porous sheet for the purpose of introducing the exhaust gas to the electrode 15, and the shielding layer 13 is formed from a dense layer made to suppress the transmission of the exhaust gas. The diffusion resistance layer 12 has a mixing chamber 17 formed therein to surround the electrode 15.

Each of the diffusion resistance layer 12 and the shielding layer 13 is made of ceramics such as alumina, spinel or zirconia according to a sheet formation method, and its gas permeability depends on the average pore size and the porosity.

The insulating layer 14 is made of highly heat-conductive ceramics such as alumina, and an atmosphere duct 18 is formed in a portion of the insulating layer 14 facing the electrode 16. The insulating layer 14 has a heater 19 embedded therein. The heater 19 comprises a linear heating device which generates heat when energized by a battery power supply, and the heat generation heats the entire sensor element 10.

With the sensor element 10 thus constructed, an exhaust gas existing around the sensor element 10 is introduced through side portions of the diffusion resistance layer 12, then flows through the diffusion resistance layer 12 into the mixing chamber 17, and reaches the electrode 15. When the exhaust gas is in a lean condition, the oxygen in the exhaust gas is decomposed at the electrode 15 and discharged from the electrode 16 into the atmosphere duct 18. On the other hand, when the oxygen in the exhaust gas is in a rich condition, the oxygen in the atmosphere duct is decomposed at the electrode 16 and discharged through the electrode 15.

Figure 3:
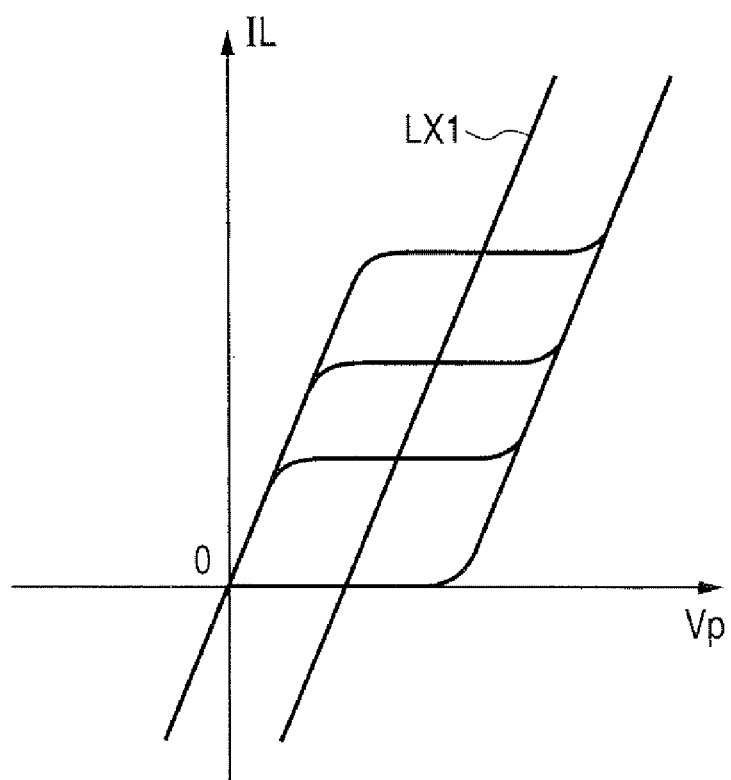
FIG. 3 is a graph showing an output characteristic (V-I characteristic) of the sensor element.

FIG. 3 is a graph showing an output characteristic (V-I characteristic) of the sensor element 10. In FIG. 3, a straight line portion (flat portion) of the output characteristic curve extending parallel to the voltage axis Vp (horizontal axis) forms a limiting current region specifying an element current IL (limiting current) of the sensor element 10, and an increase/decrease in the element current IL corresponds to an increase/decrease in air-fuel ratio (that is, the degree of lean/rich condition). Stated in other words, the element current IL increases as the air-fuel ratio shifts toward the lean side, while the element current IL decreases as the air-fuel ratio shifts toward the rich side. In FIG. 3, LX1 represents an applied voltage characteristic line (applied voltage map set in a manner as to assume a first-order straight line) for determining an applied voltage Vp to the sensor element 10, and the inclination or slope of the applied voltage characteristic line LX1 generally corresponds to the slope of a resistance dominant region (which extends to a lower voltage side from the limiting current region formed by the flat straight line portion).

Referring back to FIG. 1, a description will be given below of an electric configuration of a sensor control circuit forming a sensor control apparatus according to the present exemplary embodiment. The sensor control circuit 20 shown in FIG. 1 includes an applied voltage control circuit 21 connected to one terminal (positive terminal S+ connected to the electrode 16 shown in FIG. 2) of the sensor element 10. The applied voltage control circuit 21 includes a reference power supply 22, and a noninverting amplifier circuit 23 connected to the reference power supply 22. The noninverting amplifier circuit 23 has an operational amplifier 23a, a feedback resistance 23b and an input resistance 23c that are connected to an inverting input terminal (negative (−) input terminal) of the operational amplifier 23a, and a capacitance 24 connected in parallel to the feedback resistance 23b. With this arrangement, the noninverting amplifier circuit 23 is provided with a low-pass filter (LPF) formed integrally therewith for preventing oscillation of the applied voltage. The LPF has a cutoff frequency fc of 2.7 Hz, for example.

The sensor control circuit 20 also includes an alternating current (AC) power supply circuit 26, a buffer 27 and a current measurement resistance 28 that are connected in series to the other terminal (negative terminal S-connected to the electrode 15 shown in FIG. 2) of the sensor element 10.

The AC power supply circuit 26 is an AC voltage generating means or device for generating an AC voltage at a frequency ranging from 10 to 20 kHz, for example, and is comprised of an AC voltage generating circuit, and a low-pass filter (LPF) for filtering an AC voltage output from the AC voltage generating circuit. The AC power supply circuit 26 applies an AC voltage to the sensor element 10.

The current measurement resistance 28 is provided on an electric path extending between the AC power supply circuit 26 and the sensor element 10, and one terminal of the current measurement resistance 28 which is on the side opposite to the sensor element 10, is held at a reference voltage (center voltage of the AC voltage supplied from the AC power supply circuit 26). An element current is measured at an intermediate point A between the current measurement resistance 28 and (the negative terminal S1 of) the sensor element 10.

Also connected to the intermediate point A, is a low-pass filter (LPF) 29 composed of a resistance and a capacitance. The LPF 29 is also connected to a noninverting input terminal (positive (+) input terminal) of the operational amplifier 23a of the noninverting amplifier circuit 23. In the illustrated arrangement, an intermediate point voltage between the current measurement resistance 28 and the sensor element 10 (that is, a voltage divided through the current measurement voltage 28 and the sensor element 10) is inputted via the LPF 29 to the noninverting amplifier circuit 23 of the applied voltage control circuit 21.

Figure 4:
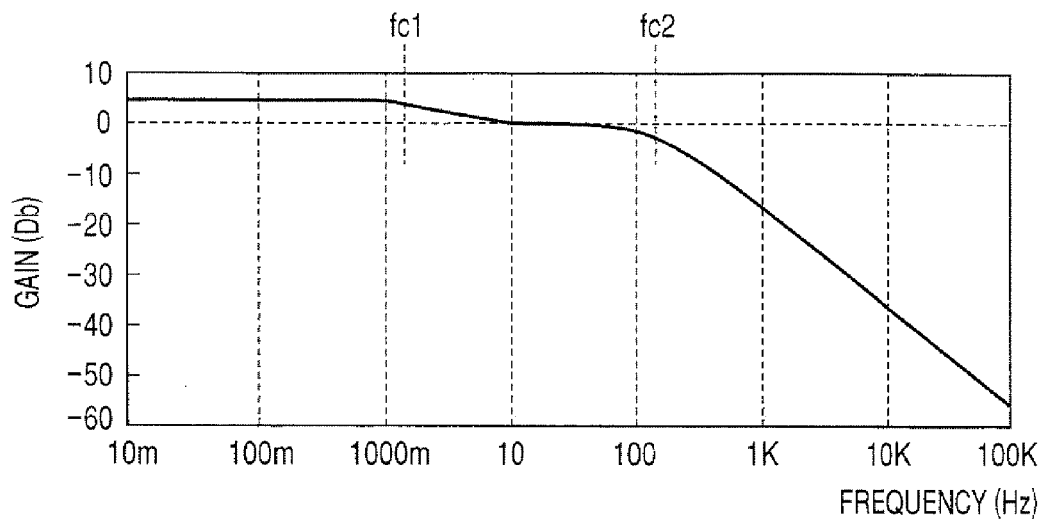
FIG. 4 is a graph showing a frequency characteristic of a low-pass filter of the sensor control apparatus.

The LPF 29 has a cutoff frequency fc of 150 Hz, for example. The aforesaid applied voltage oscillation preventing LPF (formed integrally with the noninverting amplifier circuit 23) and the LPF 29 used in combination are able to realize a frequency characteristic shown in FIG. 4. In FIG. 4, reference character fc1 denotes the cutoff frequency of the LPF formed integrally with the noninverting amplifier circuit 23 and the reference character fc2 denotes the cutoff frequency of the LPF 29.

In the applied voltage control circuit 21, the reference power supply 22 corresponds to a voltage applying section for the detection of an air-fuel ratio and, in the illustrated embodiment, this circuit 21 outputs a fixed voltage of 2.6 V. The AC power supply circuit 26 corresponds to a voltage applying section for the detection of an impedance and, in the illustrated embodiment, this circuit 26 outputs an AC voltage having an amplitude of 1 V on both positive and negative sides of a reference voltage 2.2 V. Noise removal capacitances 31 and 32 are connected to the positive and negative terminals (S+ and S−) of the sensor element 10.

At the intermediate point A between the current measurement resistance 28 and (the negative terminal S− of) the sensor element 10, there are provided two signal output sections arranged to individually take in or introduce the intermediate point voltage (divided voltage which is divided through the current measurement resistance 28 and the sensor element 10). One of these signal output sections is an A/F signal output section 41, and the other signal output section is an impedance signal output section 42. The A/F signal output section 41 includes an operational amplifier 43 and a low-pass filter (LPF) section 44 that are integrated with each other to form a noninverting amplifier circuit. In the A/F signal output section 41, the intermediate point voltage (also called "point A voltage") is inputted through the LPF 29 to a noninverting input terminal (positive (+) input terminal) of the operational amplifier 43. In this instance, a varying component of the point A voltage, which varies in an alternating fashion for impedance detection, is removed. In the illustrated embodiment, in order to simplify the circuit configuration, the LPF 29 provided on the applied voltage feedback path is used also for the purpose of removing the AC variations from the A/F signal. The impedance signal output section 42 is constituted by a high-pass filter (HPF) 45 and a peak hold circuit 46. The peak hold circuit 46 includes a signal amplifier section formed integrally therewith.

An A/F detection signal outputted from the A/F signal output section 41 and an impedance detection signal outputted from the impedance signal output section 42 are inputted to a microcomputer 48. The microcomputer 48 is a known arithmetic device equipped with a CPU, various memories, and an A/D converter in which the A/F detection signal and the impedance detection signal (both analog signals) are inputted.

At the A/F signal output section 41 and the impedance signal output section 42, the voltage signal is amplified. In this instance, amplification factors of the respective signal output sections 41 and 42 are set individually in accordance with voltage levels of the A/F signal component and the impedance signal component and a voltage processing range (from 0 to 5 V in the illustrated embodiment) of the A/D converter of the microcomputer 48. In the illustrated embodiment, the amplification factor of the A/F signal output section 41 is set to be 10 to 20, and the amplification factor of the impedance signal output section 42 is set to be 5.

In the sensor control circuit 20 of the foregoing construction, an AC voltage is applied from the AC power supply circuit 26 to the sensor element 10 whereupon an element current, which is a combination of a current component corresponding to an A/F (oxygen concentration in the exhaust gas) and a current component corresponding to an impedance of the sensor element 10, flows through the sensor element 10. In this instance, a voltage appearing at the intermediate point A between the current measurement resistance 28 as a measurement point for an A/F detection signal and an impedance detection signal periodically alters its polarity at a frequency of the sensor applied voltage (frequency of the AC voltage). Then, at the LPF 29 and the A/F signal output section 41, a current component (DC component) of the element current corresponding to a current A/F is extracted from the voltage at the intermediate point between the current measurement resistance 28 and the sensor element 10, and the extracted current component (DC component) corresponding to the current A/F is amplified at a predetermined amplification factor and subsequently outputted as an A/F detection signal into the microcomputer 48.

On the other hand, at the impedance signal output section 42, a current component (AC component) of the element current corresponding to a current element impedance is extracted from the voltage at the intermediate point between the current measurement resistance 28 and the sensor element 10, and a peak value of the extracted current component (AC component) corresponding to the current element impedance is output as an impedance detection signal into the microcomputer 48. The microcomputer 48 calculates an A/F (oxygen concentration in the exhaust gas) and an element impedance, respectively, on the basis of the A/F detection signal and the impedance detection signal.

In the voltage signal measured at the intermediate point A between the current measurement resistance 28 and the sensor element 10, an A/F signal component and an impedance signal component differ in voltage level. However, since the voltage signal is introduced through separate routes into the A/F signal output section 41 and the impedance signal output portion 42, and the introduced signal components are amplified separately, it is possible to eliminate a difficulty involved in another technique such that amplification based on the A/F signal component lowers the impedance detection accuracy, and amplification based on the impedance signal component affects the A/F detection accuracy.

The sensor element 10 can be expressed by way of an equivalent circuit as a series circuit having a resistance component and a capacitance component, and its frequency characteristic (sensor characteristic) has a high-pass filter (HPF) characteristic. In this case, if the total gain including the gain of the sensor element 10 (sensor gain) and the gain of the sensor control circuit 20 (circuit gain) is greater than "1", the oscillation of the applied voltage occurs. Thus, in order to prevent the occurrence of the applied voltage oscillation, an LPF characteristic is provided as a frequency characteristic of the sensor control circuit 20. In this instance, a total characteristic is the sum of the sensor characteristic and the circuit characteristic. The gain of the total characteristic is made smaller than "1" to thereby suppress oscillation of the applied voltage.

Figure 5:
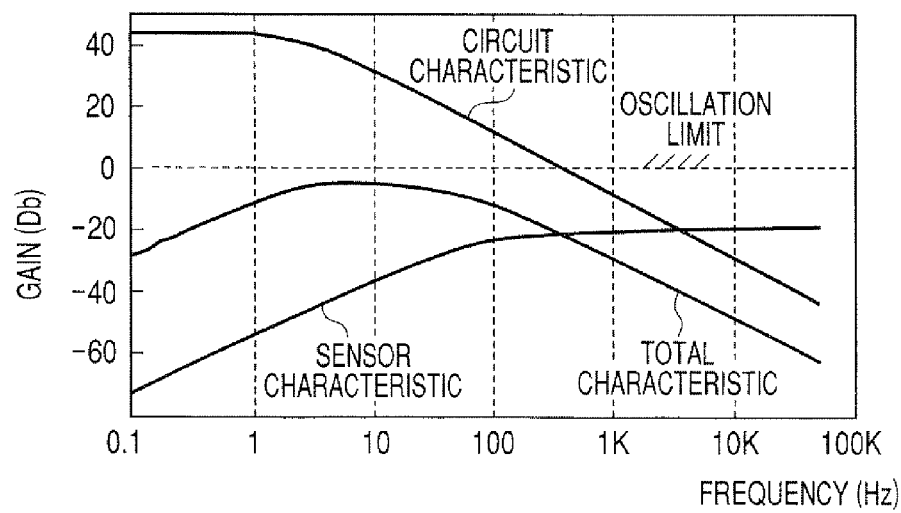
FIG. 5 is a graph showing frequency characteristics of various structural components of the sensor control apparatus.

FIG. 5 shows frequency characteristics of the sensor element 10, the sensor control circuit 20 and a combination of the sensor element 10 and the sensor control circuit 20 (that is, the sensor characteristic, circuit characteristic and total characteristic). As described above, the sensor characteristic has an HPF characteristic, and the circuit characteristic has an LPF characteristic. Thus, the gain of the total characteristic is smaller than "1" (oscillation limit).

In the sensor element 10, the individual variability or deterioration with age may cause a variation in sensor capacitance, which can lead to a gain variation occurring in the applied voltage control. In the illustrated embodiment, when the sensor capacitance variation occurs, the gain variation is suppressed for the reason described below in detail.

Figure 6:
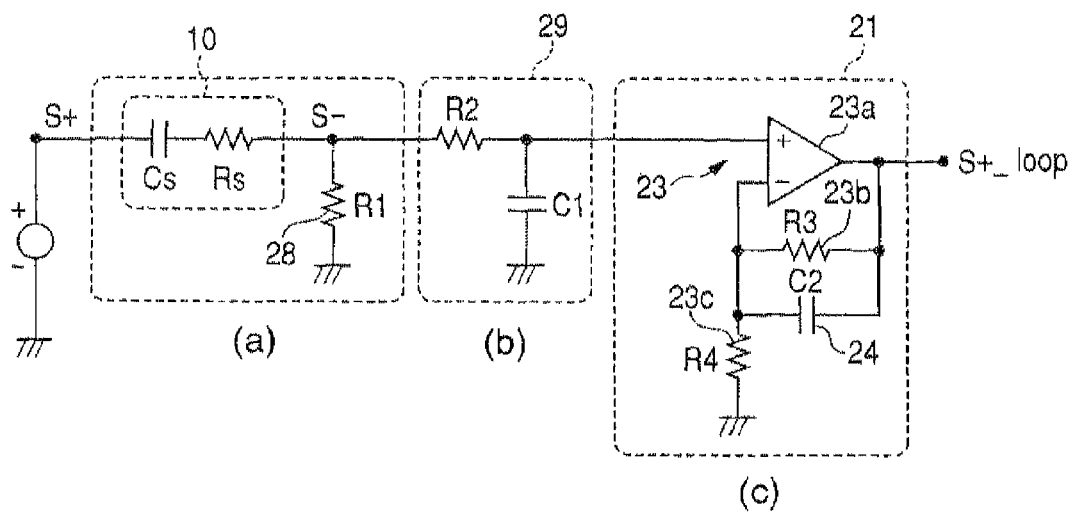
FIG. 6 is a circuit diagram showing an equivalent circuit of an applied voltage loop portion of the sensor control apparatus.

The sensor control circuit 20 has an applied voltage loop portion that can be expressed by an equivalent circuit shown in FIG. 6. In FIG. 6, Cs represents the sensor capacitance component (capacitive reactance), Rs represents a resistance value, R1 represents the resistance value of the current measurement resistance, R2 represents the resistance value of the LPF 29, R3 and R3 represent resistance values of the resistances 23b and 23c of the noninverting amplifier circuit 23, and C2 represents the capacitance of the capacitor 24. The equivalent circuit shown in FIG. 6 is expressed by a frequency transfer function represented by the following Equation (9).

$$G(j\omega) = \left(\frac{R_1}{R_1 + R_s + \frac{1}{j\omega C_s}}\right) \times \left(\frac{1}{1 + j\omega C_1 R_2}\right) \times \left(1 + \frac{R_3}{R_4}\frac{1}{1 + j\omega C_2 R_3}\right) \quad (9)$$

In Equation (9), the first, second and third terms on the right-hand side correspond to three circuit portions in broken-lined blocks (a), (b) and (c) shown in FIG. 6. Referring to Equation (9), calculating a gain characteristic as an amplitude ratio gives Equation (10) below.

$$|G(j\omega)| = \frac{R_1}{\sqrt{(R_1 + R_s)^2 + \left(\frac{1}{\omega C_s}\right)^2}} \times \frac{1}{\sqrt{1 + (\omega C_1 R_2)^2}} \times \frac{\sqrt{(R_3 + R_4)^2 + (\omega C_2 R_3 R_4)^2}}{R_4\sqrt{1 + (\omega C_2 R_3)^2}} \quad (10)$$

Figure 7:
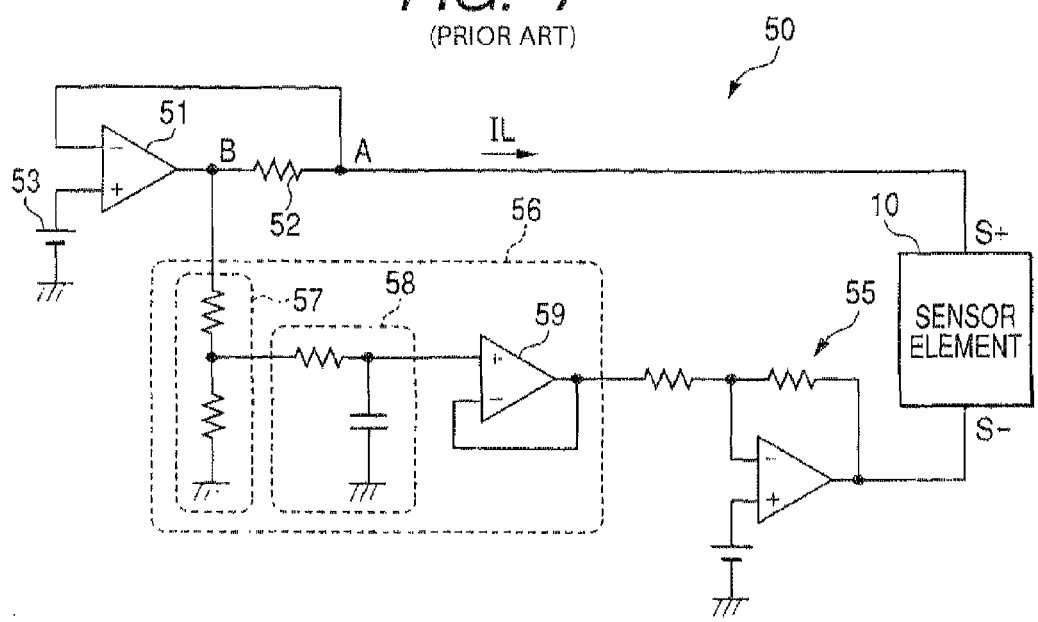
FIG. 7 is a circuit diagram showing, for comparative purposes, the general configuration of a conventional sensor control circuit.

For comparative purposes, a configuration of a conventional sensor control circuit 50 will be described below with reference to FIG. 7. In FIG. 7, the configuration of an applied voltage control system of the conventional sensor control circuit 50 is illustrated.

In the sensor control circuit 50, a positive terminal S+ of a sensor element 10 is connected via an operational amplifier 51 and a current measurement resistance (shunt resistance) 52 to a reference power supply 53 as in a manner shown in FIG. 7. A negative terminal S− of the sensor element 10 is connected via an inverting amplifier circuit 55 to an applied voltage control circuit 56. Point A at one end of the current measurement resistance 52A is held at a reference voltage (for example, 2.2 V) of the reference power supply 53. An element current IL flows through the current measurement resistance 52, and the voltage at a point B is variable with the element current IL.

The applied voltage control circuit 56 monitors the point B voltage, determines a voltage to be applied to the sensor element 10 on the basis of a value of the monitored point B voltage, and variably controls the sensor applied voltage. In the applied voltage control circuit 56, a voltage dividing circuit 57 composed of two resistances is connected to the point B (element current measurement point), and a voltage-dividing point (intermediate point) of the voltage-dividing circuit 57 is connected to a low-pass filter (LPF) 58 and a buffer 59. The LPF 58 is composed of a resistance and a capacitor.

Figure 8:
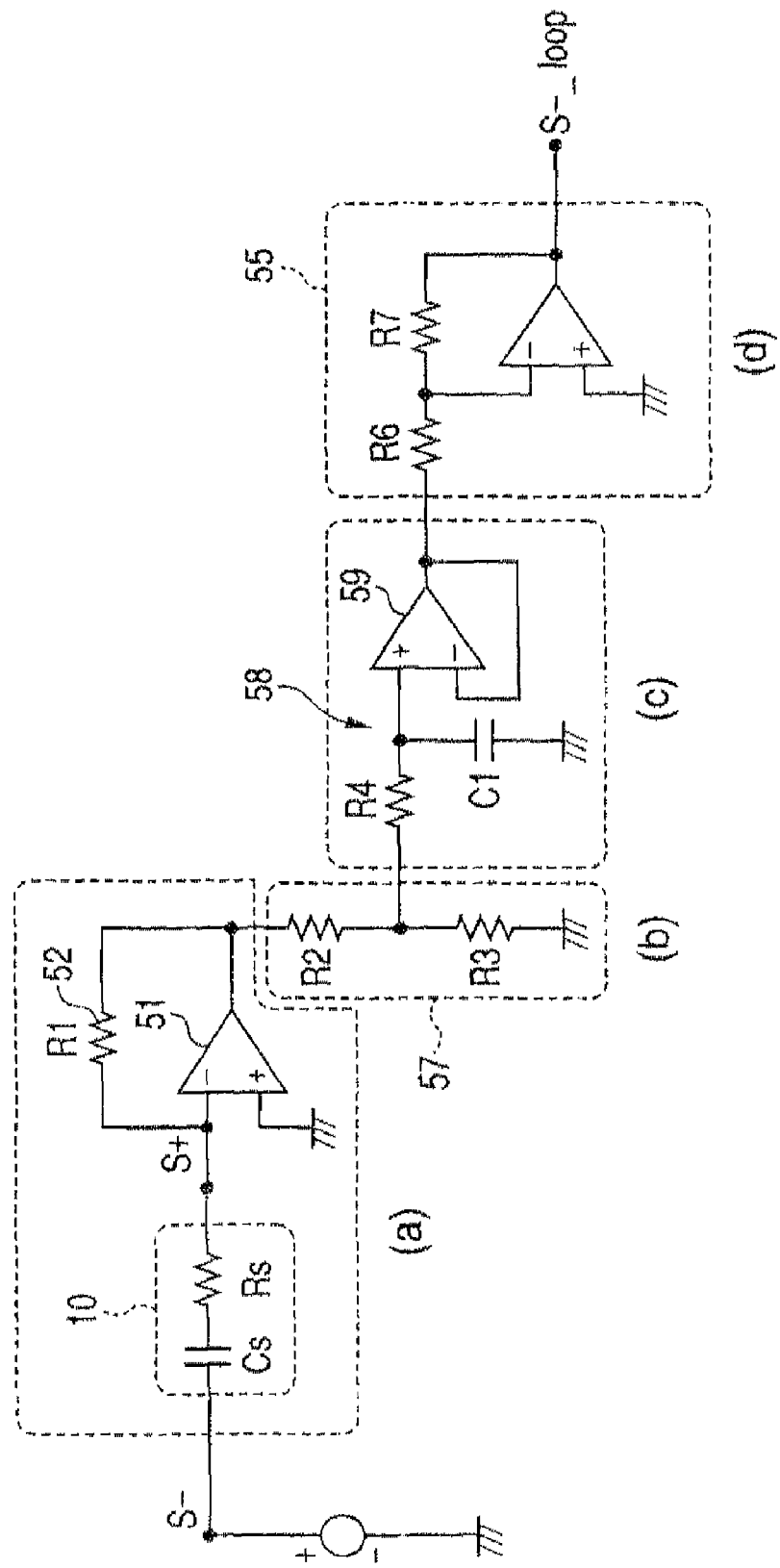
FIG. 8 is a circuit diagram showing an equivalent circuit of an applied voltage loop portion of the sensor control apparatus.
Figure 9A:
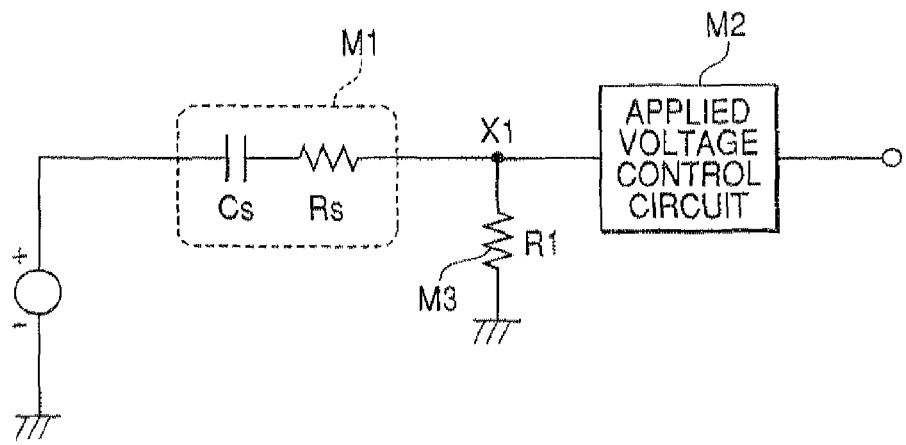
FIG. 9(a) is a circuit diagram showing an equivalent circuit provided for the purpose of explanation of features of the sensor control apparatus of the present invention.
Figure 9B:
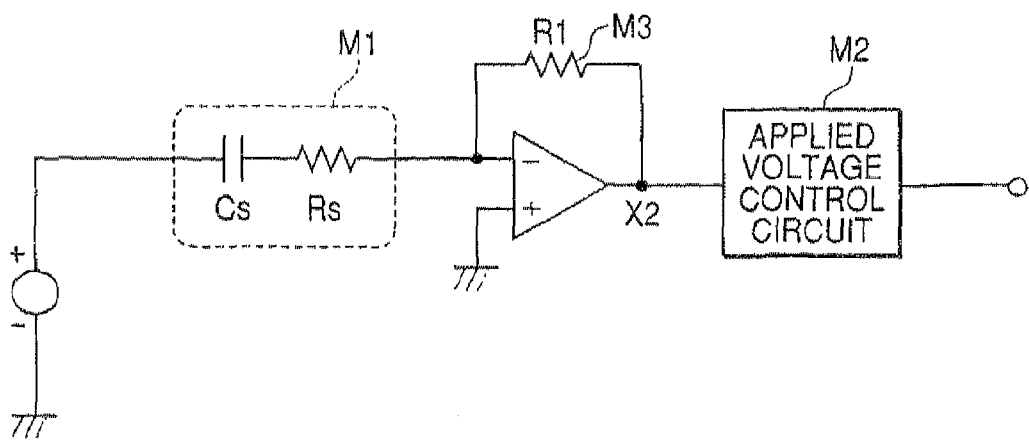
FIG. 9(b) is a view similar to FIG. 9(a) but showing an equivalent circuit of the conventional sensor control apparatus.

Regarding the sensor control circuit 50 shown in FIG. 7, an equivalent circuit of the applied voltage loop portion is shown in FIG. 8. In FIG. 8, Cs represents the sensor capacitance component (capacitive reactance), Rs represents the sensor resistance component, R1 represents the resistance value of the current measurement resistance 52, R2 and R3 represent the resistance values of the respective resistances of the voltage-dividing circuit 57, R4 represents the resistance value of the LPF 58, and C1 represents the capacitance value. Thus, the equivalent circuit shown in FIG. 8 can be expressed by a frequency transfer function shown in Equation (11) below. In the inverting amplifier circuit 55, the resistance value R6 is equal to the resistance value R7, and an amplification factor (gain) is set to be "1".

$$G(j\omega) = \left(-\frac{R_1}{R_s + \frac{1}{j\omega C_s}}\right) \times \left(\frac{R_3}{R_2 + R_3}\right) \times \left(\frac{1}{1 + j\omega C_1 R_4}\right) \times (-1) \quad (11)$$

In Equation (11), the first, second, third and fourth terms on the right-hand side correspond to four circuit portions in broken-lined blocks (a), (b), (c) and (d) shown in FIG. 8. Referring to Equation (11), calculating a gain characteristic as an amplitude ratio gives Equation (12) below.

$$|G(j\omega)| = \frac{R_1}{\sqrt{R_s^2 + \left(\frac{1}{\omega C_s}\right)^2}} \times \frac{R_3}{R_2 + R_3} \times \frac{1}{\sqrt{1 + (\omega C_1 R_4)^2}} \times 1 \quad (12)$$

$$= \frac{Rg}{\sqrt{R_s^2 + \left(\frac{1}{\omega C_s}\right)^2}} \times \frac{1}{\sqrt{1 + (\omega C_1 R_4)^2}}$$

In Equation (12), $Rg = R_1 \times R_3/(R_2 + R_3)$. Rg corresponds to a slope of inclination of an applied voltage characteristic line LX in the applied voltage control circuit 56.

Next, the gain characteristic (Equation (10)) in the sensor control circuit 20 according to the preferred embodiment of the invention and the gain characteristic (Equation (12)) in the conventional sensor control circuit 50 will be compared for verification thereof. More specifically, (A) an element current extracting portion and (B) an applied voltage oscillation preventing LPF portion of each of the inventive and conventional sensor control circuits 20 and 50 will be described separately with respect to differences in the gain characteristic. The element current extracting portion corresponds to a circuit portion in a broken-lined block (a) shown in each of FIG. 6 and FIG. 8, and the applied voltage oscillation preventing LPF portion corresponds to a circuit portion in a broken-lined block (c) in each of FIG. 6 and FIG. 8.

(A) Element Current Extracting Portion:

A structural difference is in that in case of the inventive sensor control circuit 20 shown in FIG. 1, an element current signal is measured at an intermediate point (voltage-dividing point) between the sensor element 10 and the current measurement resistance 28, whereas in case of the conventional sensor control circuit 50 shown in FIG. 7, the element current is measured by the current measurement resistance 52 through a current-to-voltage conversion process.

In each of Equations (10) and (12), the first term on the right-hand side corresponds to a gain characteristic of the element current extracting portion. In case of the conventional sensor control circuit 50, the first denominator term of the gain characteristic (Equation (12)) is represented by an impedance of the sensor element, which is shown as being divided into a resistance component and a reactance component. This means that the gain characteristic is fully dependent on the impedance of the sensor element (first denominator term in Equation (12)). It is therefore considered that the gain can be varied with a variation in the sensor capacitive reactance.

On the other hand, in case of the inventive sensor control circuit 20, the first denominator term of the gain characteristic (Equation (10)) contains not only a sensor resistance component Rs but also a resistance value R1 of the current measurement resistance 28. This means that the value of a voltage divided through the sensor element resistance component and the resistance value R1 of the current measurement resistance 28 is reflected into the gain characteristic. Thus, the effect of the sensor capacitive reactance on the gain characteristic is reduced and, hence, the gain variation can be suppressed even when sensor capacitive reactance variation occurs.

(B) Applied Voltage Oscillation Preventing LPF Portion:

A structural difference is in that in case of the inventive sensor control circuit 20 shown in FIG. 1, a low-pass filter (LPF) is provided integrally with the noninverting amplifier circuit 23 serving as an applied voltage output section, whereas in case of the conventional sensor control circuit 50 shown in FIG. 7, a low-pass filter (LPF) 58 is provided separately from an inverting amplifier circuit 55 serving as an applied voltage output section at a front stage of the inverting amplifier circuit 55.

In Equation (10), the third term on the right-hand side corresponds to a gain characteristic of the applied voltage oscillation preventing LPF portion. Similarly, in Equation (12), the second term in a lower part as simplified by substitution with Rg. In case of the conventional sensor control circuit 50, only the denominator term in the lower second term of the gain characteristic (Equation (12)) contains a capacitance (C1) of the capacitor in the LPF 58. Accordingly, if variation occurs in the capacitance of the capacitor in the LPF 58, the performance will be degraded by the effect of the capacitance variation and, in the worst case, oscillation of the applied voltage will occur.

By contrast, in case of the inventive sensor control circuit 20, the third term of the gain characteristic (Equation (10))

contains a capacitance (C2) of the capacitor in the LPF (oscillation prevention LPF) at both the denominator and the numerator. Accordingly, even when variation occurs in the capacitance of the capacitor in the LPF, the effect of the capacitance variation can be suppressed. This will ensure that the LPF can be provided without involving performance degradation caused due to component variations.

The inventive sensor control circuit 20 and the conventional sensor control circuit 50 are further verified for actual gain variation. The verification is made using a frequency band (for example, 10 Hz) where oscillation is likely to occur in a high-pass filter (HPF) characteristic of the sensor element 10.

In Equation (10) representing the gain characteristic of the inventive sensor control circuit 20, if Rs=28Ω, (1/ωCs) =80.4Ω, R1=200Ω, R3=300 kΩ. R4=400 kΩ and C2=0.22 µF, the gain characteristic (|G(jω)|) can be obtained in the following manner. In this instance, ωC2·R3=4.147, and in the second term of Equation (10), ωC1·R2=0.063 and hence the second term is nearly equal to 1 and can thus be ignored.

$$|G(j\omega)|_{f=10\,Hz} = \frac{200}{\sqrt{(200+28)^2 + 80.4^2}} \times \frac{1}{\sqrt{1+0.063^2}} \times$$

$$\frac{\sqrt{(300k+400\,k)^2 + (4.147 \times 400\,k)^2}}{400\,k\sqrt{1+4.147^2}}$$

$$= 0.82726 \times 1.0588$$

$$= 0.876$$

Now, considering that the capacitance C2 of the oscillation preventing LPF (which is integrated with the noninverting amplifier circuit 23) of the sensor control circuit 20 varies from 0.22 µF to 0.1683 µF, the gain characteristic (|G(jω)|) can be obtained in the following manner. In this instance, ωC2·R3=3.172.

$$|G(j\omega)|_{f=10\,Hz} = \frac{200}{\sqrt{(200+28)^2 + 80.4^2}} \times \frac{1}{\sqrt{1+0.063^2}} \times$$

$$\frac{\sqrt{(300k+400\,k)^2 + (3.172 \times 400\,k)^2}}{400\,k\sqrt{1+3.172^2}}$$

$$= 0.82726 \times 1.0892$$

$$= 0.901$$

It appears clear from the foregoing that a change in the capacitance C2 of the oscillation preventing LPF from 0.22 µF to 0.1683 µF causes the gain to vary from 0.876 to 0.901. In this instance, the gain has increased by 3 percent (i.e., 0.901/0.876=1.03).

By contrast, in Equation (12) representing the gain characteristic of the conventional sensor control circuit 50, if Rs=28Ω, (1/ωCs)=80.4Ω, Rg=150Ω, (R1=200Ω, R2=16.91Ω and R3=50 kΩ) and C1=0.22 µF, the gain characteristic (|G(jω)|) can be obtained in the following manner. In this instance, ωC1·R4=5.529.

$$|G(j\omega)|_{f=10\,Hz} = \frac{150}{\sqrt{28^2 + 80.4^2}} \times \frac{1}{\sqrt{1+5.529^2}}$$

$$= \frac{150}{85.1} \times \frac{1}{5.62}$$

$$= 0.314$$

Now, considering that the capacitance C1 of the oscillation preventing LPF 58 of the conventional sensor control circuit 50 varies from 0.22 µF to 0.1683 µF, the gain characteristic (|G(jω)|) can be obtained in the following manner. In this instance, ωC1·R4=4.23.

$$|G(j\omega)|_{f=10\,Hz} = \frac{150}{\sqrt{28^2 + 80.4^2}} \times \frac{1}{\sqrt{1+4.23^2}}$$

$$= \frac{150}{85.1} \times \frac{1}{4.346}$$

$$= 0.406$$

As appears clear from the foregoing, a change in the capacitance C1 of the oscillation preventing LPF 58 from 0.22 µF to 0.1683 µF causes the gain to vary from 0.314 to 0.406. In this instance, the gain has increased by 29 percent (i.e., 0.406/0.314=1.29).

It will be appreciated from the comparison made between the inventive sensor control circuit 20 and the conventional sensor control circuit 50 that a variation in the gain caused due to the same change in capacitance of the capacitor in the oscillation preventing LPF (from 0.22 µF to 0.1683 µF) is smaller in the inventive sensor control circuit 20 than in the conventional sensor control circuit 50. As evidenced from the numeric data discussed above, the inventive sensor control circuit 20 is able to sufficiently suppress the gain variation caused due to component variations.

According to the embodiment of the invention just described above, various advantageous effects can be attained as enumerated below.

Because in the sensor control circuit 20, an element current signal is measured at an intermediate point (voltage-dividing point) between the sensor element 10 and the current measurement resistance 28, and the measured element current signal is fed back to the applied voltage control circuit 21, the effect of a sensor capacitance component on the gain characteristic is reduced to the extent that a change in the gain can be effectively suppressed even when a variation in the sensor capacitance component occurs. As a result, even if the sensor capacitance component varies due to individual difference, deterioration with age or the like, the applied voltage to the sensor element 10 can be controlled with high accuracy. This will ensure that adequate sensor control can be achieved over a wide A/F detection range.

Furthermore, since an oscillation preventing low-pass filter (LPF) is provided integrally with the noninverting amplifying circuit 23 forming an applied voltage output section, even when the variation in capacitance of a capacitor of the LPF occurs, the effect of the capacitance variation can be reduced. This will ensure that the LPF can be provided without involving performance degradation caused due to component variations. Thus, oscillation of the applied voltage can be controlled as desired.

By thus suppressing the performance degradation caused due to component variations, it is possible to reduce the capacitance of the capacitor. This will lead to reductions in size and cost of the sensor control circuit 20.

By virtue of the AC power supply circuit 26 connected to the current measurement resistance 28, the detection of an element impedance can be performed continuously as long as an AC voltage generated from the AC power supply circuit 26 is applied to the sensor element 10.

Furthermore, since the voltage at the intermediate point between the current measurement resistance 28 and the sensor element 10 is taken or introduced through separate routes into the A/F signal output section 41 and the impedance signal output section 42, even when a voltage signal corresponding to an A/F and a voltage signal corresponding to an element impedance have different voltage levels, it is possible to perform suitable signal processing operations (amplification, for example) individually for the respective voltage signals. In this instance, detection of the A/F can be performed without requiring a two-stage amplification. As a result, the A/F detection and the impedance detection can be achieved with a high degree of accuracy.

Concerning the A/F detection and the impedance detection, the intermediate point voltage (divided voltage) between the current measurement resistance 28 and the element resistance 10 is used to measure a voltage signal. Unlike another conventional technique in which a voltage appearing across the current measurement resistance is used for measuring a voltage signal, this arrangement allows for direct introduction of the voltage signal without requiring a current-to-voltage converting means such as a differential amplifier. By thus obviating the need for a differential amplifier in connection with the A/F detection and the impedance detection, it is possible to simplify the circuit configuration.

Furthermore, since the A/F signal output section 41 and the impedance signal output section 42 amplify the respective inputted voltage signals individually at different amplification factors, it is possible to amplify the A/F detection signal and the impedance detection signal as desired by a signal processing range of an A/D converter of the microcomputer 48. This will increase the resolution of the A/F detection and the impedance detection.

The present invention should by no means be limited to the illustrated embodiment described above, but may be practiced in other ways as well, for example, in the following manners.

Although in the illustrated embodiment, the applied voltage control circuit 21 includes a noninverting amplifier circuit 23, an inverting amplifier circuit can be used in place of the noninverting amplifier circuit 23. In the latter case, a capacitor is provided in parallel with a feedback resistance of an operational amplifier forming the inverting amplifier circuit, so as to provide a low-pass filter (LPF) integrally with the inverting amplifier circuit.

In the illustrated embodiment, the voltage at the intermediate point between the current measurement resistance 28 and the sensor element 10 is introduced through separate routes into the A/F signal output section 41 and the impedance signal output section 42 for the detection of an A/F and an impedance. This arrangement can be modified. For example, an element current signal (a converted voltage at the intermediate point between the current measurement resistance 28 and the sensor element 10) is commonly taken in or introduced for the A/F detection and the impedance detection, and at an intermediate stage of signal processing operation (for instance, after the signal has been amplified), the element current signal is separated into an A/F detection signal and an impedance detection signal.

The AC power supply circuit 26 may be arranged to output an AC voltage either continuously or as necessary. For example, the AC power supply circuit 26 may be arranged to output an AC voltage intermittently at an impedance detection frequency defined by predetermined regular intervals of time.

In the embodiment described above, the sensor element 10 has a construction shown in FIG. 2. The invention can be applied to another sensor element having a different element construction. For example, in place of the sensor element of the single-cell type, a sensor element of the double-cell type having a pump cell and an electromotive force cell may be used. In other words, the sensor element having a single-layer solid electrolytic member may be substituted by a sensor element having double-layer or three-layer solid electrolytic construction. Furthermore, without being limited to the sensor element having a multilayer construction, the present invention is also applicable to a sensor element having a cup-like construction.

Moreover, the present invention is also applicable to other than the A/F sensors for detecting the oxygen concentration, i.e., a gas concentration sensor for detecting other gas concentrations. For example, a complex gas concentration sensor includes a plurality of cells made from a solid electrolyte, and of these cells, a first cell (pump cell) discharges or pumps out oxygen in a measured gas (detection gas) and detects the oxygen concentration and a second cell (sensor cell) detects a gas concentration of a specific component in the gas after the oxygen discharged. This gas concentration sensor is actually used, for example, as an NOx sensor for detecting an NOx concentration in an exhaust gas, and when the present invention is applied thereto, the NOx concentration detection accuracy can be improved. Yet, the present invention is also applicable to a gas concentration sensor having a plurality of cells including, in addition to the aforesaid first and second cells, a third cell (monitor cell, or second pump cell) for detecting a residual oxygen concentration after the oxygen discharge.

The present invention is also applicable to a gas concentration sensor which can detect an HC concentration or a CO concentration as a gas concentration of a specific component. In this case, the excess oxygen in a detection gas is discharged by the pump cell and HC or CO in the gas after the excess oxygen discharge is decomposed by the sensor cell to detect an AC concentration or a CO concentration.

Without being limited to the gas sensor (sensor elements) used in a gasoline engine, the sensor control apparatus according to the present invention is also applicable to a gas sensor (sensor element) used in other types of engines such as a diesel engine. Furthermore, when the sensor control apparatus of the invention is used in combination with a gas sensor other than for vehicles, a gas other than the exhaust gas becomes a detection gas (measured gas).

Obviously, various minor changes and modifications are possible in the light of the above teaching. It is to be understood that within the scope of the appended claims the present invention may be practiced otherwise than as specifically described.

What is claimed is:

1. A sensor control apparatus for use with a sensor element as a controlled object having a solid electrolytic layer and capable of producing an element current responsive to a concentration of a particular component of a measured gas when a voltage is applied to the sensor element, the sensor element having resistance and capacitance included therein, the sensor control apparatus comprising:

an applied voltage control circuit for variably controlling the voltage applied to the sensor element; and a current measurement resistance having one terminal connected to the sensor element and having another terminal connected to a reference voltage in a current path over which the element current flows when the voltage is applied to the sensor element under the control of the applied voltage control circuit, wherein an intermediate voltage representing an amount of the element current is measured at an intermediate point where the voltage applied to the sensor element is divided by the resistance of the sensor element and the current measurement resistance, wherein the applied voltage control circuit includes an inverting or a noninverting amplifier circuit to which the intermediate voltage appearing at the intermediate point between the sensor element and the current measurement resistance is inputted, and a capacitor connected in parallel to a feedback resistance of an operational amplifier of the amplifier circuit, and the applied voltage control circuit being feed-back controlled based on the intermediate voltage in a feed-back loop where the sensor element, the current measurement resistance, a filter circuit and the amplifier circuit are connected with each other, and wherein the applied voltage control circuit determines the applied voltage to the sensor element based on the intermediate voltage.

2. A sensor control apparatus according to claim 1, wherein an oscillation preventing circuit to avoid oscillation of the voltage applied to the sensor element is provided, the oscillation preventing circuit including the current measurement resistance, the filter circuit and a low-pass filter integrated with the amplifier circuit.

3. A sensor control apparatus according to claim 1, wherein the current measurement resistance is connected to an AC power supply circuit, which outputs an AC voltage periodically changing its polarity with respect to the reference voltage.

4. A sensor control apparatus according to claim 3, further comprising:

a first signal output section which extracts from the intermediate voltage appearing at the intermediate point between the sensor element and the current measurement resistance, a first current component corresponding to gas concentration in a measured gas and outputs the extracted first current component to an arithmetic device; and a second signal output section which extracts from the intermediate voltage appearing at the intermediate point between the sensor element and the current measurement resistance, a second current component corresponding to a resistance component of the sensor element and outputs the extracted second current component to the arithmetic device, wherein the intermediate voltage is introduced through separate routes into the first and second signal output sections.

5. A sensor control apparatus according to claim 4, wherein the first signal output section and said second signal output section include amplifier circuit sections for amplifying the intermediate voltage inputted respectively thereto, the amplifier circuit sections having amplification factors that are individually set.

6. A sensor control apparatus according to claim 4, wherein the first signal output section includes a filter means for extracting only a direct current component of the intermediate voltage, and an amplifying means for amplifying the intermediate voltage based on a voltage-processing range of a signal input section of the arithmetic device.

7. A sensor control apparatus according to claim 4, wherein the second signal output section includes a filter means for extracting only an alternating current component of a voltage measured at the intermediate point between the sensor element and the current measurement resistor and a peak detecting means for detecting a peak value of the alternating current component extracted by the filter means of the second signal output section.

* * * * *